(12) United States Patent
Chen et al.

(10) Patent No.: US 8,263,130 B2
(45) Date of Patent: Sep. 11, 2012

(54) HOLLOW SPHERE FROM AMPHIPHILIC CHITOSAN DERIVATIVES AND METHOD OF PREPARING AMIPHIPHILIC CHITOSAN DERIVATIVE COMPLEX FOR MEDICAL USE

(75) Inventors: San-Yuan Chen, Hsinchu (TW); Kun-Ho Liu, Hualien (TW); Dean-Mo Liu, Jhubei (TW)

(73) Assignee: National Chiao Tung University, Hsinchu (TW)

( * ) Notice: Subject to any disclaimer, the term of this patent is extended or adjusted under 35 U.S.C. 154(b) by 425 days.

(21) Appl. No.: 12/379,880

(22) Filed: Mar. 4, 2009

(65) Prior Publication Data

US 2010/0098731 A1  Apr. 22, 2010

(30) Foreign Application Priority Data

Oct. 16, 2008  (TW) .............................. 97139732 A

(51) Int. Cl.
*A61K 9/14* (2006.01)
(52) U.S. Cl. ...................................................... 424/489
(58) Field of Classification Search .................. None
See application file for complete search history.

(56) References Cited

OTHER PUBLICATIONS

Masotti, A novel method to obtain chitosan DNA nanospheres and a study of their release properties, Nanotechnology, 2008, 19, 55302-55308.*

Kun, Ho Liu, at al. "Self-Assembled Hollow nanocapsule from Amphiphatic Carboxymethyl-Hexanoyl Chitosan as Drug Carrier"; Macromolecules, Aug. 8, 2008; p. 6511-6516; vol. 41; 2008 American Chemical Society.

* cited by examiner

*Primary Examiner* — Paul Dickinson
(74) *Attorney, Agent, or Firm* — Bacon & Thomas, PLLC

(57) ABSTRACT

A hollow sphere from amphiphilic chitosan derivatives and a method of preparing an amphiphilic chitosan derivative complex for medical use are disclosed, and the hollow sphere from amphiphilic chitosan derivatives comprises: chitosan derivatives represented by the following formula (I), which self-assemble and form a hollow sphere in a solvent;

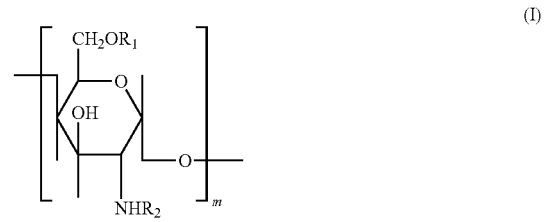

wherein, each $R_1$ is independently hydrogen, $C_1$~$C_4$ alkyl, $C_1$~$C_6$ carboxyl, sulfate group, or phosphate group, each $R_2$ is independently hydrogen, $C_1$~$C_{12}$ alkyl, $C_1$~$C_6$ carboxyl, or $C_2$~$C_{12}$ acyl group, and m is an integer of 100-2000.

10 Claims, 2 Drawing Sheets

HOLLOW SPHERE FROM AMPHIPHILIC CHITOSAN DERIVATIVES AND METHOD OF PREPARING AMIPHIPHILIC CHITOSAN DERIVATIVE COMPLEX FOR MEDICAL USE

BACKGROUND OF THE INVENTION

1. Field of the Invention

The present invention relates to a hollow sphere from amphiphilic chitosan derivatives and a method of preparing an amphiphilic chitosan derivative complex for medical use and, more particularly, to a hollow sphere from amphiphilic chitosan derivatives and a method of preparing an amphiphilic chitosan derivative complex for medical use, which can be applied for anticancer drug delivery.

2. Description of Related Art

Currently, anticancer drug carriers have developed for anticancer chemotherapy, and liposome is considered to be an ideal drug carrier due to its unique properties to target cancer. Especially, the liposome encapsulates drugs and releases drugs at a tumor area but does not pass through normal tissue, so that the probability of destroying normal cells can be reduced. However, the liposome shows low encapsulation efficiency, high-priced processing, insufficient stability, and poor biocompatibility, so that there are still some problems in applying the liposome in the clinical treatment. Hence, there has been some research in natural polymers with good biocompatibility, in order to develop an efficient drug carrier system for anticancer chemotherapy.

Among the well-known natural polymers, chitosan is considered to be able to be applied on drug carriers, due to its low cost, high biocompatibility, and degradability. Generally, chitosan is derived from chitin by removing acetyl groups. This process, called deacetylation, release amino groups and gives the chitosan a cationic characteristic. The formula of the chitosan is represented as follows:

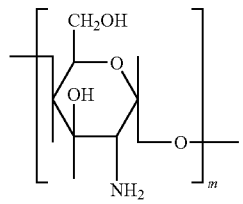

The chitosan has advantages of low price and good biocompatibility, and the double layer structure of the liposome is considered to be an ideal form for drug carriers. Hence, if the chitosan can be processed and form a double layer structure similar to the liposome, it is possible to apply the double layer structure made from the chitosan to the carriers for drug delivery efficiently. Presently, the double layer structure made from the chitosan is synthesized by template-coating or layer-by-layer building. However, the aforementioned methods have the disadvantages of complicated processing and high cost, so that it is difficult to be commercialized.

Therefore, it is desirable to develop a drug carrier for anticancer chemotherapy, which has a double layer structure similar to the liposome and the characteristics of the chitosan, such as low cost, high biocompatibility, and degradability.

SUMMARY OF THE INVENTION

The object of the present invention is to provide a hollow sphere from amphiphilic chitosan derivatives, which is formed through the self-assembling of the amphiphilic chitosan derivatives. Moreover, the hollow sphere from the amphiphilic chitosan derivatives of the present invention can be used for drug carriers of anticancer chemotherapy.

Another object of the present invention is to provide a method of preparing amphiphilic chitosan derivative complex for medical use, and an active component can be effectively encapsulated inside a hollow sphere self-assembling from the amphiphilic chitosan derivatives. At the same time, the encapsulation efficiency for the active component can be improved by the method of preparing the present invention.

To achieve the aforementioned objects, the hollow sphere from amphiphilic chitosan derivatives of the present invention includes: chitosan derivatives represented by the following formula (I), which self-assemble and form a hollow sphere in a solvent;

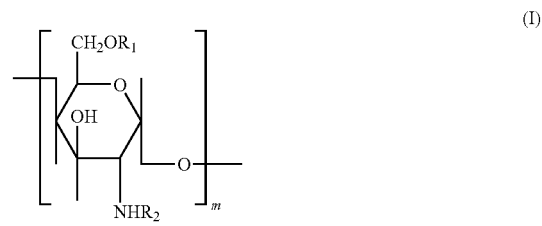

wherein, each $R_1$ independently is hydrogen, $C_1$~$C_4$ alkyl, $C_1$~$C_6$ carboxyalkyl, sulfate ($-SO_3$), or phosphate ($-H_2PO_4$); each $R_2$ independently is hydrogen, $C_1$~$C_{12}$ alkyl, $C_1$~$C_6$ carboxyalkyl, or $C_2$~$C_{12}$ acyl; and m is an integral of 100~2000.

In addition, the present invention also provides a method of preparing an amphiphilic chitosan derivative complex for medical use, comprising following steps: (A) providing a chitosan, and substituting at least one hydrophilic group, and at least one hydrophobic group on the chitosan to obtain chitosan derivatives; (B) dissolving the chitosan derivatives in a solvent to obtain a solution of the chitosan derivatives; and (C) mixing the solution of the chitosan derivatives, and active components, to form hollow spheres through the self-assembling of the chitosan derivatives, wherein the active components are encapsulated inside the hollow spheres.

The amphiphilic chitosan derivatives of the present invention can be substituted with hydrophilic groups and hydrophobic groups on the chitosan at the same time, because the chemical modification of the chitosan can be easily accomplished. Beside, the amphiphilic chitosan derivatives can self-assemble to form a hollow sphere with a double layer structure similar to the liposome, i.e. hydrophilic-hydrophobic-hydrophilic configuration, due to the hydrophobicity of the amphiphilic chitosan derivatives. Additionally, the hollow structure of the hollow sphere can improve the drug loading of the active components. Moreover, the outer layer of the hollow sphere from the amphiphilic chitosan derivatives of the present invention has hydrophilicity, so the biocompatibility and the affinity for water can be improved, and the harm to normal tissue can be reduced at the same time. Furthermore, the hollow sphere from the amphiphilic chitosan derivatives and the amphiphilic chitosan derivative complex for medical of the present invention have the advantages of simple processability, low cost, and high biocompatibility, so it is possible to replace the liposome as drug carriers.

According to the hollow sphere from the amphiphilic chitosan derivatives and the method of preparing the amphiphilic chitosan derivative complex for medical use of the present invention, each $R_1$ of the chitosan derivatives of formula (I) independently may be hydrogen, carboxymethyl, carboxyl, sulfate, phosphate, trimethyl, or succinyl. Preferably, each $R_1$ independently is hydrogen, or carboxymethyl.

According to the hollow sphere from amphiphilic chitosan derivatives and the method of preparing the amphiphilic chitosan derivative complex for medical use of the present invention, each $R_2$ of the chitosan derivatives of formula (I) independently may be hydrogen, $C_1$~$C_{12}$ alkyl, $C_1$~$C_6$ carboxyalkyl, $C_2$~$C_{12}$ acyl, tosyl, phthaloyl, or silyl. Preferably, each $R_2$ independently is hydrogen, carboxymethyl, or $C_2$~$C_{12}$ acyl. More preferably, each $R_2$ independently is hydrogen, or $C_2$~$C_{12}$ acyl.

According to the hollow sphere from amphiphilic chitosan derivatives and the method of preparing the amphiphilic chitosan derivative complex for medical use of the present invention, the chitosan derivatives are compounds represented by the following formula (II), means the percentage of substituting the amino groups of the chitosan with the hydrophobic groups.

In addition, according to the method of preparing the amphiphilic chitosan derivative complex for medical use of the present invention, the step (C) further may be: mixing and sonicating the solution of the chitosan derivatives, and active components, to form hollow spheres through the self-assembling of the chitosan derivatives, wherein the active components are encapsulated inside the hollow spheres.

Furthermore, according to the method of preparing the amphiphilic chitosan derivative complex for medical use of the present invention, the active component is a drug.

Other objects, advantages, and novel features of the invention will become more apparent from the following detailed description when taken in conjunction with the accompanying drawings.

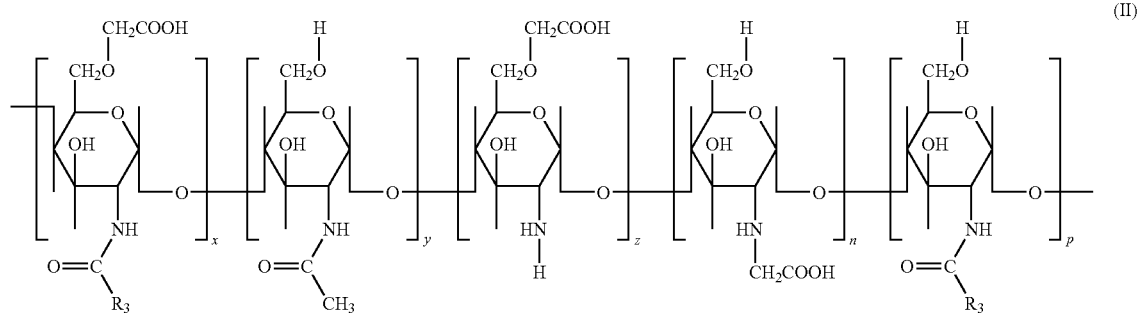

wherein, each $R_3$ independently is $C_5$~$C_{11}$ alkyl; and x, y, z, n, and p independently are integrals of 20~2000.

According to the hollow sphere from amphiphilic chitosan derivatives and the method of preparing the amphiphilic chitosan derivative complex for medical use of the present invention, the hollow sphere has a mean size of 10~500 nm.

According to the hollow sphere from amphiphilic chitosan derivatives and the method of preparing the amphiphilic chitosan derivative complex for medical use of the present invention, the solvent may be water solution, organic solvent, or any mixture solution.

According to the hollow sphere from amphiphilic chitosan derivatives and the method of preparing the amphiphilic chitosan derivative complex for medical use of the present invention, the temperature for self-assembling of chitosan derivatives may be 0~80° C.

According to the method of preparing the amphiphilic chitosan derivative complex for medical use of the present invention, the chitosan has the molecular weight of 1000-400,000 g/mol. In addition, the deacetylation degree of the chitosan is 65%~100%. Herein, "deacetylation degree" means the percentage of removing the acetyl groups on the chitin.

According to the method of preparing the amphiphilic chitosan derivative complex for medical use of the present invention, the hydrophilic group may be selected from the group consisting of carboxymethyl, carboxyl, sulfate, phosphate, trimethyl, and succinyl, and the hydrophobic group may be selected from the group consisting of $C_1$~$C_{12}$alkyl, $C_2$~$C_{12}$acyl, tosyl, phthaloyl, or silyl.

According to the method of preparing the amphiphilic chitosan derivative complex for medical use of the present invention, the substitution degree of the hydrophobic group is 5~100%. Herein, "substitution degree of hydrophobic group"

DETAILED DESCRIPTION OF THE PREFERRED EMBODIMENT

Comparative Example 1

Figure 1:
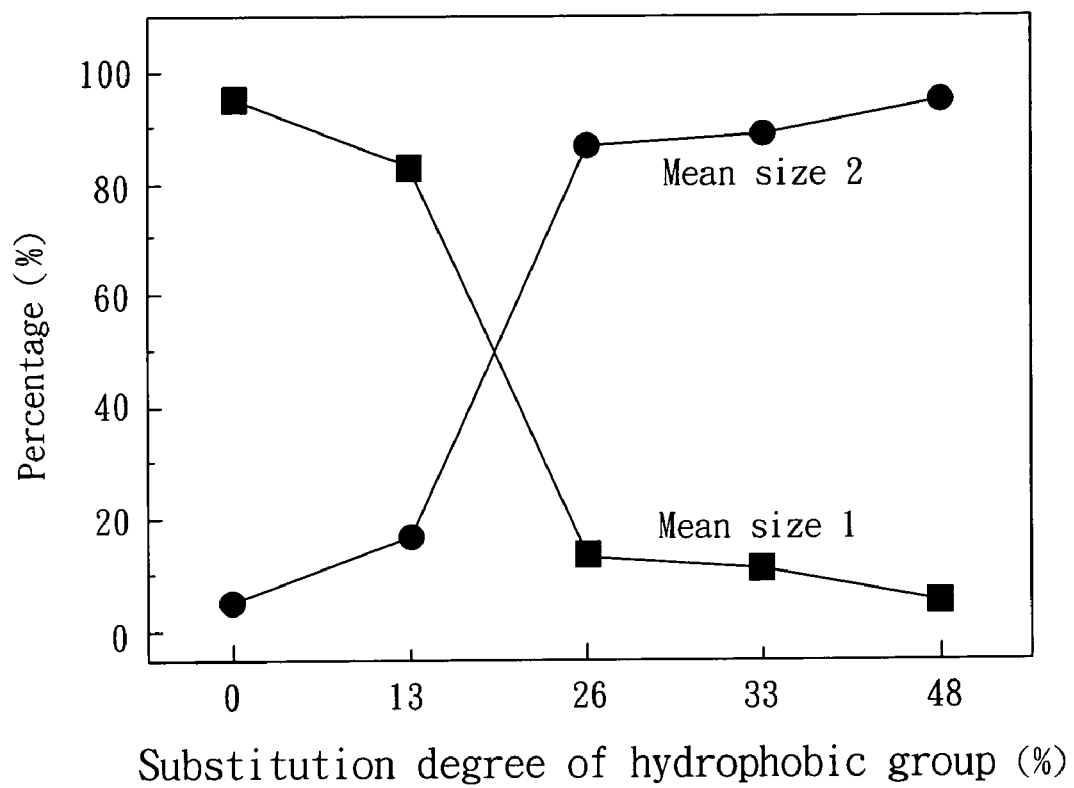
FIG. 1 is a diagram illustrating the relation between the substitution degree of hydrophobic group and the mean size of the hollow sphere from the amphiphilic chitosan derivatives of the present invention.

Synthesis of Chitosan Derivatives with Hydrophilic Carboxymethyl Modification 5 g of chitosan (Mw=215,000 g/mol, deacetylation degree=80-90%, Adrich-Sigma) was suspended in 2-propanol (50 mL) at room temperature while being stirred for 30 min. The resulting suspension was gently mixed with 12.5 mL of NaOH solution to obtain a mixture, and the substitution degree of hydrophilic group can be adjusted by the concentration of NaOH in the mixture. Herein, the mixture contained 13.3 M NaOH. Then, the mixture was reacted with chloroacetic acid, followed by drying, to obtain soluble carboxymethyl-modified chitosan sample.

Embodiment 1

Synthesis of Chitosan Derivatives with Hydrophobic Hexanoyl Modification and Hydrophilic Carboxymethyl Modification 2 g of dried chitosan derivatives with hydrophilic carboxymethyl modification prepared in Comparative example 1 was dissolved in distilled water (50 mL) while being stirred for 24 hours. Then, the resulting solution was mixed with methanol (50 mL), followed by the addition of hexanoyl anhydride at concentration of 0.2 M to obtain a reaction solution. After reacting for 20 hours, the reaction solution was collected by dialysis with ethanol solution (25% v/v) for 24 hours. After dying the resulting solution, chitosan derivatives with hydrophobic hexanoyl modification and hydrophilic carboxymethyl modification, called amphiphilic chitosan derivatives, were obtained, which can be represented by the following formula (II). In addition, the sites of the substitution groups and the degree of hexanoyl substitution were confirmed by $^1$H NMR and elemental analysis for N content. In the present embodiment, the degree of hexanoyl substitution of the chitosan derivatives is 13%.

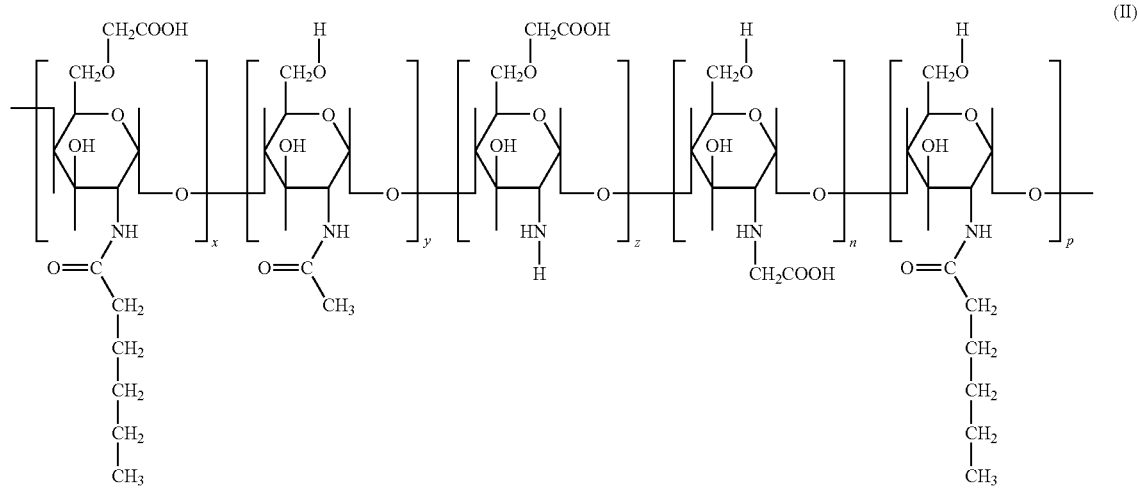

(II)

Embodiment 2

The reaction condition and steps in the present embodiment are the same as those in Embodiment 1, except that the concentration of the hexanoyl anhydride is 0.4 M. The degree of hexanoyl substitution of the chitosan derivatives prepared in the present embodiment is 26%.

Embodiment 3

The reaction condition and steps in the present embodiment are the same as those in Embodiment 1, except that the concentration of the hexanoyl anhydride is 0.5 M. The degree of hexanoyl substitution of the chitosan derivatives prepared in the present embodiment is 33%.

Embodiment 4

The reaction condition and steps in the present embodiment are the same as those in Embodiment 1, except that the concentration of the hexanoyl anhydride is 1.0 M. The degree of hexanoyl substitution of the chitosan derivatives prepared in the present embodiment is 48%.

Embodiment 5

The reaction condition and steps in the present embodiment are the same as those in Embodiment 1, except that hexanol anhydride is substituted with decanoic anhydride. The degree of decanoyl substitution of the chitosan derivatives prepared in the present embodiment is 12%.

Embodiment 6

The reaction condition and steps in the present embodiment are the same as those in Embodiment 2, except that hexanol anhydride is substituted with decanoic anhydride. The degree of decanoyl substitution of the chitosan derivatives prepared in the present embodiment is 24%.

Embodiment 7

The reaction condition and steps in the present embodiment are the same as those in Embodiment 3, except that hexanol anhydride is substituted with decanoic anhydride. The degree of decanoyl substitution of the chitosan derivatives prepared in the present embodiment is 34%.

Embodiment 8

The reaction condition and steps in the present embodiment are the same as those in Embodiment 4, except that hexanol anhydride is substituted with decanoic anhydride. The degree of decanoyl substitution of the chitosan derivatives prepared in the present embodiment is 45%.

Embodiment 9

2 g of dried chitosan derivatives with hydrophilic carboxymethyl modification prepared in Comparative example 1 was dissolved in distilled water (50 mL) while being stirred for 24 hours. Then, the resulting solution was mixed with methanol (50 mL), followed by the addition of dodecanoic anhydride at concentration of 0.2 M to obtain a reaction solution. The reaction solution was reacted under 50° C. for 20 hours, followed by being reacted at room temperature for 18 hours, and then the reaction solution was collected by dialysis with ethanol solution (25% v/v) for 24 hours. After dying the resulting solution, a chitosan derivatives with hydrophobic dodecanoyl modification and hydrophilic carboxymethyl modification, called amphiphilic chitosan derivatives were obtained. In addition, the sites of the substitution groups and the degree of dodecanoyl substitution were confirmed by $^1$H NMR and elemental analysis for N content. In the present embodiment, the degree of dodecanoyl substitution of the chitosan derivatives is 10%.

Embodiment 10

The reaction condition and steps in the present embodiment are the same as those in Embodiment 9, except that the concentration of the dodecanoic anhydride is 0.4 M. The degree of dodecanoyl substitution of the chitosan derivatives prepared in the present embodiment is 22%.

Embodiment 11

The reaction condition and steps in the present embodiment are the same as those in Embodiment 9, except that the concentration of the dodecanoic anhydride is 0.5 M. The degree of dodecanoyl substitution of the chitosan derivatives prepared in the present embodiment is 30%.

Embodiment 12

The reaction condition and steps in the present embodiment are the same as those in Embodiment 9, except that the concentration of the dodecanoic anhydride is 1.0 M. The degree of dodecanoyl substitution of the chitosan derivatives prepared in the present embodiment is 44%.

Preparation of Hollow Spheres from Amphiphilic Chitosan Derivatives 100 mg/ml of chitosan derivatives prepared by Comparative example 1 and Embodiments 1-12 was suspended in a distilled water under gentle shaking at room temperature for 24 hours, followed by ultrasonication using a probe type sonifier (Automatic Ultrasonic Processor UH-500A) for 2 min. After repeating the sonication three times, the final products were obtained.

In order to identify whether the products were in a form of sphere, Transmission Electron Microscopy (TEM) (JEOL2100, Japan) was used to check the shape of the products and determine the size of the products. According to TEM image, it can be found that the amphiphilic chitosan derivatives can self-assemble to form hollow spheres with nano or micro sizes, through the interaction between the hydrophobic groups, wherein the hollow spheres have a double layer structure, i.e. hydrophilic-hydrophobic-hydrophilic configuration.

Characterization of the Hollow Spheres from the Amphiphilic Chitosan Derivatives The mean size and size distribution of the hollow spheres from the amphiphilic chitosan derivatives prepared by Comparative example 1 and Embodiments 1-4 were measured by dynamic light scattering (DLS) Nanoparticle Size Analyzer (LB-550, HORIBA, Japan). In addition, the critical aggregation concentration (CAC) of the amphiphilic chitosan derivatives was obtained from the fluorescent spectrum, wherein pyrene was used as a fluorescence probe due to its high affinity to hydrophobic micro-domains. The smaller of the critical aggregation concentration means the easier of forming hollow spheres. The characters of the mean size and the critical aggregation concentration of the hollow spheres from the amphiphilic chitosan derivatives are shown in Table 1.

TABLE 1

| | Hydrophobic group | Substitution degree of hydrophobic group | $CAC \times 10^{-2}$ (mg/mL) | Mean size 1 (nm) | Mean size 2 (nm) |
|---|---|---|---|---|---|
| Comparative example 1 | — | 0% | 25.0 | 19.8 ± 1.2 | 189.2 ± 2.4 |
| Embodiment 1 | Hexanoyl | 13% | 9.21 | 21.5 ± 1.6 | 210.5 ± 1.9 |
| Embodiment 2 | Hexanoyl | 26% | 3.17 | 22.3 ± 0.7 | 209.3 ± 1.4 |
| Embodiment 3 | Hexanoyl | 33% | 0.91 | 22.9 ± 1.1 | 210.9 ± 0.7 |
| Embodiment 4 | Hexanoyl | 48% | 0.40 | 23.5 ± 0.7 | 222.7 ± 2.0 |
| Embodiment 5 | Decanoyl | 12% | 6.20 | — | — |
| Embodiment 6 | Decanoyl | 24% | 1.80 | — | — |
| Embodiment 7 | Decanoyl | 34% | 0.57 | — | — |
| Embodiment 8 | Decanoyl | 45% | 0.36 | — | — |
| Embodiment 9 | Dodecanoyl | 10% | 5.00 | — | — |
| Embodiment 10 | Dodecanoyl | 22% | 1.20 | — | — |
| Embodiment 11 | Dodecanoyl | 30% | 0.36 | — | — |
| Embodiment 12 | Dodecanoyl | 44% | 0.32 | — | — |

From the results shown in Table 1, the amphiphilic chitosan derivatives can form two kinds of hollow spheres with different mean sizes. As the substitution degree of hydrophobic group increases, the amphiphilic chitosan derivatives tend to form hollow spheres with mean size 2. FIG. 1 shows the relation between the substitution degree of hydrophobic group and mean size distribution. As shown in FIG. 1, most of the amphiphilic chitosan derivatives prepared in Embodiments 3 and 4 form hollow spheres with a particle size of 200 nm.

Measurement of the Thickness of the Shells of the Hollow Spheres from the Amphiphilic Chitosan Derivatives In order to confirm the amphiphilic chitosan derivatives forming hollow spheres, the hollow spheres from the amphiphilic chitosan derivatives were dehydrated to remove water inside and outside the hollow spheres. Then, Scanning Electron-Microscopy (SEM) (S6500, JEOL, Japan) was used for detecting the dehydrated hollow spheres from amphiphilic chitosan derivatives. SEM image shows that the hollow spheres with particle size of 200 nm each lost their structural integrity, and collapsed to resemble a flattened basketball after dehydration. Furthermore, the thickness of the double shell is about 9 nm, which can be found from SEM image, so the thickness of the single shell is calculated to be about 4.5 nm.

Figure 2:
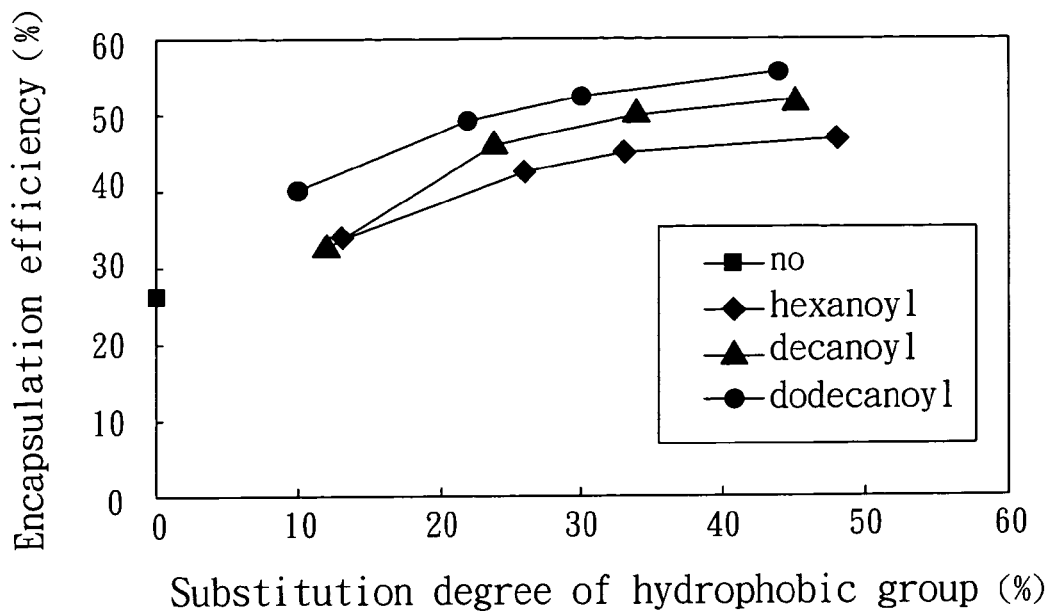
FIG. 2 is a diagram illustrating the relation between the substitution degree of hydrophobic group and the encapsulation efficiency of the hollow sphere from the amphiphilic chitosan derivatives of the present invention.

Measurement of the Encapsulation Efficiency of the Hollow Sphere from Amphiphilic Chitosan Derivatives Doxorubicin (DOX) was provided and mixed with 20 mL of chitosan derivatives solution prepared by using Comparative example 1 and Embodiments 1-12, respectively. The final concentration of the DOX in the chitosan derivatives solution is 20 μg/mL. After stirring for 24 hours, the resulting solution was ultrasonicated with sonicator (Automatic Ultrasonic Processor UH-500A), and the chitosan derivatives self-assembled to form hollow spheres, wherein the DOX was encapsulated inside the hollow spheres to form an amphiphilic chitosan derivative complex for medical use. Insoluble and free DOX was removed by centrifugation at 2000 rmp under 4° C. for 5 mins. Then, the amphiphilic chitosan derivative complex for medical use was separated from the solution by centrifugation at 15000 rmp under 4° C. for 15 mins. Free DOX concentration in the supernatant was analyzed by UV-VIS spectrometer (SP-8001, Metertech Inc.). Encapsulation efficiency (EE) of the hollow sphere from amphiphilic chitosan derivatives can be calculated with the DOX concentration. Herein, encapsulation efficiency was obtained as described below:

$$EE=(A-B)/A \times 100$$

wherein, A is the total amount of the DOX, and B is the amount of DOX remaining in the supernatant. The calculation results are shown in FIG. 2, wherein X-axis is the substitution degree of hydrophobic group, and Y-axis is encapsulation efficiency. As shown in FIG. 2, as the substitution degree of hydrophobic group and the length of the side chain of the hydrophobic group are increased, the encapsulation efficiency also is improved. The improved encapsulation efficiency is caused by the increase of the hydrophobic interaction of inner shell of the hollow sphere, which can restrict the outward diffusion of DOX from the hollow sphere. Hence, the release behavior of drugs can be controlled by adjusting the substitution degree and the length of side chain of the hydrophobic group.

Figure 3:
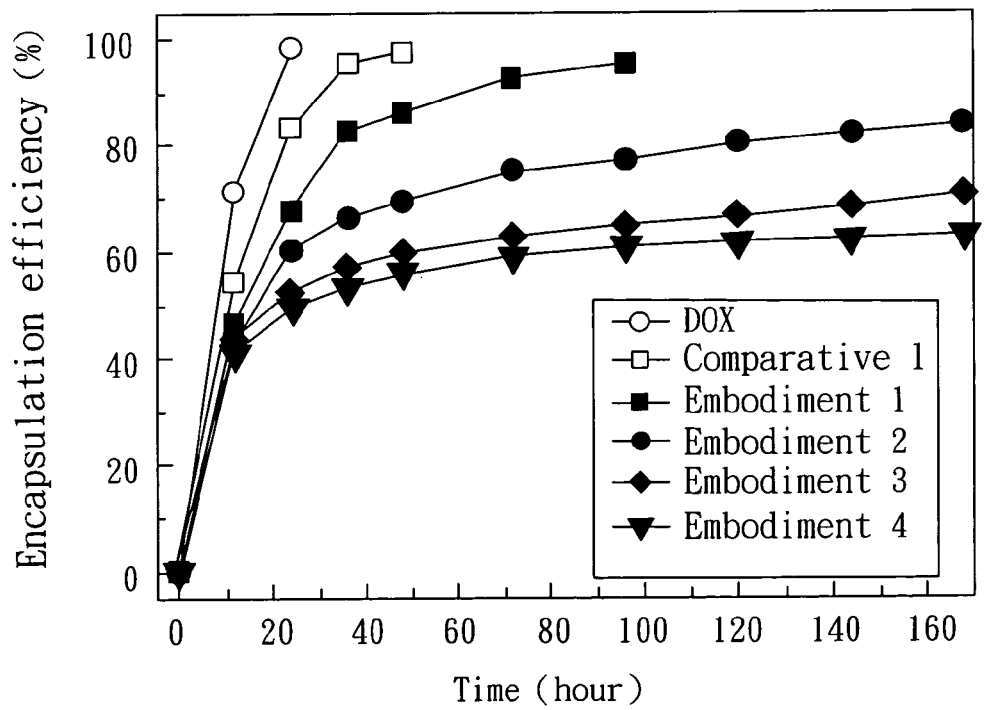
FIG. 3 is a diagram illustrating the relation between the substitution degree of hydrophobic group and the drug release percentage of the hollow sphere from the amphiphilic chitosan derivatives of the present invention.

Drug Release Behavior of the Hollow Sphere from Amphiphilic Chitosan Derivatives A solution of DOX and DOX-amphiphilic chitosan derivative complex prepared with the amphiphilic chitosan derivatives in Embodiments 1-4 was dialyzed against 0.1 M buffer (100 mL) under 37° C. The DOX concentration in the buffer was measured at various times over a 7-day period to detect the drug release behavior of the hollow spheres from the amphiphilic chitosan derivatives. The results are shown in FIG. 3, wherein X-axis is the substitution degree of hydrophobic group, and Y-axis is the releasing percentage of the DOX. As shown in FIG. 3, DOX is not easily released from the hollow spheres while the substitution degree of the hydrophobic group is increased, so that it is possible to release drugs for a long time. Hence, the drug release behavior of the hollow spheres can be controlled by adjusting the substitution degree of the hydrophobic group. Therefore, the hollow sphere from the amphiphilic chitosan derivatives of the present invention can be a suitable candidate for delivery of anticancer drugs.

In conclusion, the amphiphilic chitosan derivatives with hydrophilic and hydrophobic modification of the present invention can form hollow a sphere by self-assembling, wherein the size of the hollow sphere is about 20-200 nm, and the hollow sphere has a double layer structure, i.e. hydrophilic-hydrophobic-hydrophilic configuration. Hence, comparing with the chitosan hollow sphere prepared by template-coating or layer-by-layer building, the process of hollow sphere from chitosan derivatives is simpler and cheaper. Also, the hollow sphere from the amphiphilic chitosan derivatives of the present invention is formed through the self-assembling, so the hollow sphere can capsulate drug without destroying the drug activity. In addition, the hollow sphere from the amphiphilic chitosan derivatives of the present invention not only can maintain the stability of the active component, but also can improve the encapsulation efficiency of the hollow sphere. Furthermore, in order to control the encapsulation efficiency and the drug release behavior of the hollow sphere from the amphiphilic chitosan derivatives of the present invention, the critical aggregation concentration and surface character of the hollow sphere can be adjusted through modifying the kinds, substitution degree, and the length of the side chain of the hydrophobic group. Therefore, the hollow sphere from the amphiphilic chitosan derivatives of the present invention can be used in substitution for the liposome, and serve as the drug carriers for anticancer chemotherapy.

Although the present invention has been explained in relation to its preferred embodiment, it is to be understood that many other possible modifications and variations can be made without departing from the scope of the invention as hereinafter claimed.

What is claimed is:

1. A hollow sphere from amphiphilic chitosan derivatives comprising:

a shell which is composed of chitosan derivatives in a layer structure, wherein the chitosan derivatives are compounds represented by the following formula (II), which self-assemble and form a hollow sphere in a solvent

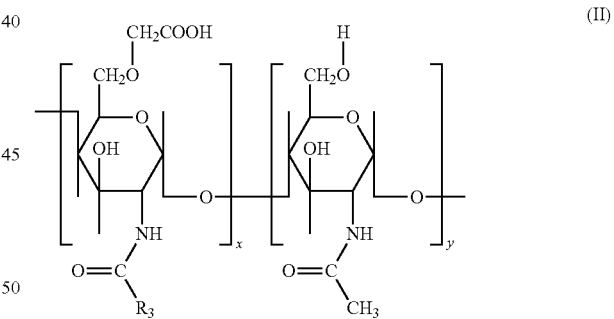

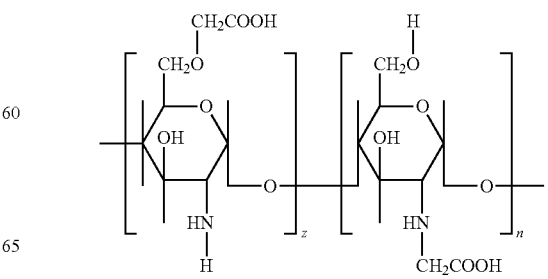

-continued

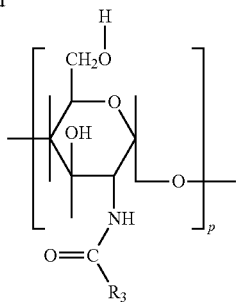

wherein, each $R_3$ independently is $C_5$~$C_{11}$ alkyl; and x, y, z, n, and p independently are integrals of 20~2000.

2. The hollow sphere from amphiphilic chitosan derivatives as claimed in claim 1, wherein the hollow sphere has a mean size of 10-500 nm.

3. The hollow sphere from amphiphilic chitosan derivatives as claimed in claim 1, wherein the shell includes a double layer structure.

4. The hollow sphere from amphiphilic chitosan derivatives as claimed in claim 1, wherein the chitosan derivatives have a substitution degree of hydropobicity of 10%-45%.

5. The hollow sphere of claim 1, which contain active drug components releaseably encapsulated within the shell.

6. A method of preparing an amphiphilic chitosan derivative of claim 1 complex for medical use, comprising following steps:
(A) providing a chitosan, and substituting at least one hydrophilic group, and at least one hydrophobic group on the chitosan to obtain chitosan derivatives;
(B) dissolving the chitosan derivatives in a solvent to obtain a solution of the chitosan derivatives; and
(C) mixing the solution of the chitosan derivatives, and active components, to form hollow spheres through the self-assembling of the chitosan derivatives, wherein the active components are encapsulated inside the hollow spheres.

7. The preparing method as claimed in claim 6, wherein the chitosan has the molecular weight of 1000~400,000 g/mol.

8. The preparing method as claimed in claim 6, wherein the deacetylation degree of the chitosan is 65-100%.

9. The preparing method as claimed in claim 6, wherein the substitution degree of the hydrophobic group is 5~100%.

10. The preparing method as claimed in claim 6, wherein the hollow sphere has a mean size of 10-500 nm.

* * * * *